United States Patent [19]

Cevasco

[11] Patent Number: 5,405,998
[45] Date of Patent: Apr. 11, 1995

[54] PROCESS FOR THE MANUFACTURE OF CYCLOALKYL AND HALOALKYL O-AMINOPHENYL KETONES

[75] Inventor: Albert A. Cevasco, Belle Meade, N.J.

[73] Assignee: American Cyanamid Company, Wayne, N.J.

[21] Appl. No.: 159,984

[22] Filed: Nov. 30, 1993

[51] Int. Cl.$^6$ .............................................. C07C 209/68
[52] U.S. Cl. .................................... 564/404; 564/395; 564/442; 564/445
[58] Field of Search ................ 564/396, 404, 395, 442

[56] References Cited

U.S. PATENT DOCUMENTS

| | | | |
|---|---|---|---|
| 3,953,510 | 4/1976 | Smith et al. | 260/580 |
| 4,160,784 | 7/1979 | Sugasawa et al. | 260/570 AB |
| 4,622,065 | 11/1986 | Van Gemert | 71/92 |
| 4,812,543 | 3/1989 | Matlack et al. | 526/281 |
| 4,988,695 | 1/1991 | Brown et al. | 514/248 |
| 5,009,699 | 4/1991 | Brady et al. | 71/92 |

OTHER PUBLICATIONS

Sugasawa, T.; Toyoda, T. Adachi, M.; and Sasakura, K., Journal Of The American Chemical Society, 100 4842 (1978).

Sugasawa, T.; Toyoda, T. Adachi, M.; Sasakura, K.; and Kitagawa, A., Journal Of Organic Chemistry, 44 578 (1979).

*Primary Examiner*—Allen J. Robinson

[57] ABSTRACT

There is provided an improved method for the production of o-aminophenyl ketones of formula I wherein R is $C_3$–$C_6$cycloalkyl or $C_1$–$C_6$haloalkyl.

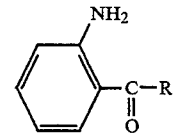

Compounds of formula I are key intermediates in the manufacture of sulfamoyl urea herbicides.

20 Claims, No Drawings

PROCESS FOR THE MANUFACTURE OF CYCLOALKYL AND HALOALKYL O-AMINOPHENYL KETONES

BACKGROUND OF THE INVENTION

Cycloalkyl and haloalkyl o-aminophenyl ketones are utilized as starting materials in the manufacture of herbicidal sulfamoyl urea derivatives. The regiospecific preparation of o-aminophenyl ketone derivatives is described in U.S. Pat. No. 4,160,784. Said patent provides a broad inclusive method to prepare a wide variety of aromatic and nonaromatic, substituted and unsubstituted o-aminophenyl ketones. However, in many instances the formation of unwanted side-products can cause decreased yields and cumbersome product isolation procedures.

Therefore, it is an-object of this invention to provide an improved process for the preparation of cycloalkyl and haloalkyl o-aminophenyl ketone which gives significantly reduced side-product formation.

It is another object of this invention to provide an improved process for the preparation of cycloalkyl and haloalkyl o-aminophenyl ketone with increased product yield.

It is a further object of this invention to provide an economic and convenient source of starting material for the manufacture of herbicidal sulfamoyl urea derivatives.

SUMMARY OF THE INVENTION

The present invention provides an improved process for the manufacture of an o-aminophenyl ketone of formula I

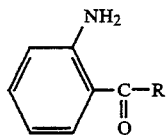

wherein R is $C_3$–$C_6$cycloalkyl or $C_1$–$C_6$haloalkyl, which comprises the following steps
  (1) reacting a nitrile of formula II

with borontrihalide in the presence of a solvent to form a 1:1 donor complex,
  (2) reacting the complex with aniline in the presence of a Lewis acid to give a reaction mixture,
  (3) sparging the reaction mixture with $N_2$ at an elevated temperature for a period of about 1–24 hours and
  (4) quenching the sparged reaction mixture with water to give the formula I product.

Compounds of formula I are useful as key intermediates in the manufacture of crop-selective sulfamoyl urea herbicides.

DETAILED DESCRIPTION OF THE INVENTION

Sulfamoyl urea derivatives are useful as herbicidal agents and in particular, 1-{[o-(cyclopropylcarbonyl)-phenyl]sulfamoyl}-3-(4,6-dimethoxy-2-pyrimidinyl)urea is useful as a potent, environmentally benign herbicide with cereal crop selectivity. An important starting material in the manufacture of this herbicide is cyclopropyl o-aminophenyl ketone or 1-(o-aminophenyl)-4-halo-1-butanone. It has now been found that cycloalkyl and haloalkyl o-aminophenyl ketones may be prepared with minimal side-product formation and in improved yield by first reacting the appropriate nitrile with borontrihalide in the presence of a solvent to form a 1:1 donor complex, second reacting the complex with aniline in the presence of a Lewis acid to form a reaction mixture, third sparging the reaction mixture with nitrogen at an elevated temperature for a period of about 1–24 hours, and fourth quenching the nitrogen-sparged reaction mixture with water. The sequential process is shown in Flow Diagram I wherein R is $C_3$–$C_6$cycloalkyl or $C_1$–$C_6$haloalkyl and X is chlorine or bromine.

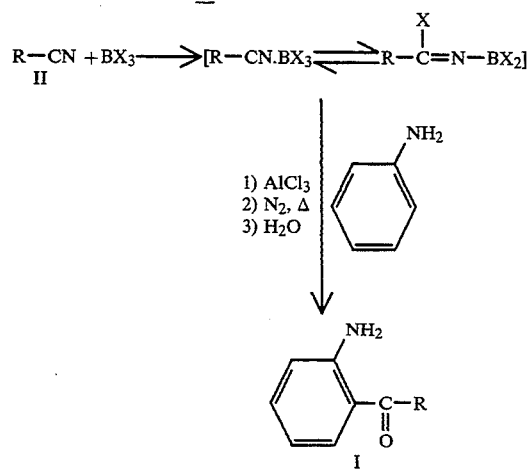

FLOW DIAGRAM I

Advantageously, the 1:1 donor complex intermediate is not isolated, but is formed in situ allowing the process to be carried out in a single reaction vessel using a common solvent system. Surprisingly, the initial formation of the 1:1 donor complex of the nitrile and borontrihalide followed by the sequential addition of aniline and a Lewis acid avoids the formation of unwanted side-products which may tie up the aniline starting material and render it unavailable to form reaction product. The introduction of the nitrogen sparge to facilitate the removal of the hydrogen chloride by-product further enhances product yield and purity by decreasing, or eliminating, acid-catalyzed side reactions. It has now been found, that on a commercial scale an external force is critical to the effective removal of the hydrogen chloride gas by-product so that side reactions and reactant degradation are avoided.

Solvents suitable for use in the process of the invention are organic solvents such as halogenated hydrocarbons, for instance methylene chloride, dichloroethane, dichloropropane and the like; aromatic hydrocarbons such as toluene, xylene, benzene and the like; halogenated aromatics such as chlorobenzene, dichlorobenzene and the like. Preferred solvents are dichloroethane, dichloropropane and toluene and the more preferred solvent is dichloroethane.

The preferred Lewis acid for use in the inventive process is aluminum chloride.

The nitrogen sparge accelerates the loss of hydrogen chloride gas and helps to drive the reaction to completion. This acceleration, and the use of an inert gas such as nitrogen, appears to be critical to enhanced product yield and quality. Reaction time during the nitrogen sparge may range from about 1–24 hours, preferably about 8–16 hours and more preferably about 12 hours.

Reaction rate increases with increased temperatures, however increased temperatures also increase reactant degradation and other undesirable side-reactions. Elevated temperatures suitable for the nitrogen sparge time period are about 30° to 150° C., preferably about 80° to 110° C.

Although stoichiometric proportions of reactants are suitable, a preferred range for the proportion of a nitrile of formula II to one molar equivalent of aniline is about 1 to 2 moles and more preferred is about 1.3 to 1.5 moles.

For a more clear understanding of the invention, specific examples thereof are set forth below. These examples are merely illustrative and are not to be understood as limiting the scope and underlying principles of the invention in any way.

The term HPLC designates high performance liquid chromatography.

EXAMPLE I

Preparation of o-aminophenyl Cyclopropyl Ketone

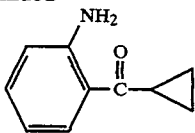

A stirred mixture of BCl$_3$ (145.2 g, 1.238 mole) in dichloroethane is treated with cyclopropylnitrile (101.8 g, 1.45 mole) over a 45 minute period at −3° to 5° C., stirred for 1 hour at 5° to 10° C., treated with aniline (112.2 g, 1.205 mole) over a 1 hour period at 7° to 12° C. stirred for 1 hour, treated with AlCl$_3$ (170.7 g, 1.281 mole) in a single portion and stirred at ambient temperatures for 1 hour. The reaction mixture is sparged with nitrogen and heated at reflux temperatures with a nitrogen sparge for 17–18 hours. The heated and sparged reaction mixture is cooled to 15° C., added to approximately a 2-fold volume of water (based upon initial reaction mixture volume) over a 30 minute period at 9° to 38° C. and stirred at 35° to 38° for 1 hour. The phases are separated and the aqueous phase is extracted with methylene chloride. The organic phases are combined and concentrated in vacuo to give the title product as an orange oil which crystallizes on standing, 149.8 g, 95.6% pure, 73.7% yield, identified by HPLC analysis.

EXAMPLE 2

Preparation of 1-(o-aminophenyl)-4-Chloro-1-Butanone

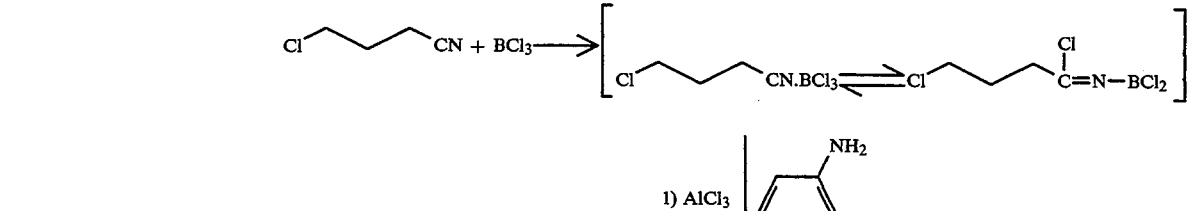

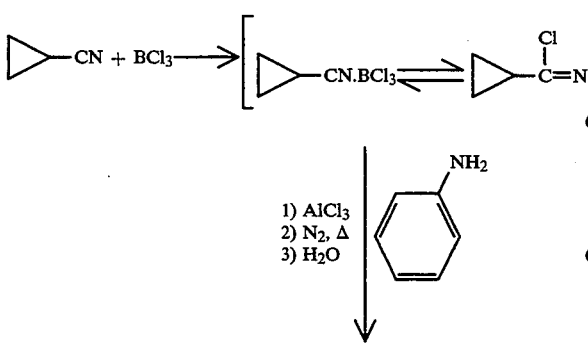

A mixture of BCl$_3$ (59.2 g, 0.50 mole) in 1,2-dichloroethane is treated with 4-chlorobutyronitrile (62.5 g, 0.604 mole) over a 1 hour period at −8° to 0° C., stirred for 1 hour at 0° to 5° C., treated with aniline (45.1 g, 0.485 mole) over a 1 hour period at 2° to 9° C., stirred for 1 hour, and treated with AlCl$_3$ (68.8 g, 0.515 mole) in a single portion at ambient temperatures. The reaction mixture is sparged with nitrogen at reflux temperature for about 17 hours. The heated and sparged reaction mixture is cooled to 35° C. and added to approximately a 2-fold volume of water (based upon initial reaction volume) and stirred for 0.5 hour at 33° to 35° C. The phases are separated and the aqueous phase is washed with 1,2-dichloroethane. The organic phases are combined and concentrated in vacuo to give a solution of the title product containing, 85.9 g of the desired o- aminophenyl ketone, 89.7% yield, identified by HPLC analysis.

EXAMPLE 3

Comparative Preparation of 1-(o-aminophenyl) Cyclopropyl Ketone

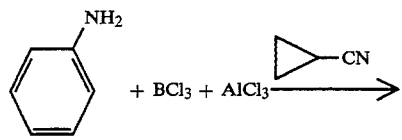

The procedure used in this example is essentially the same as that described in U.S. Pat. No. 4,160,784.

A solution of aniline (2.7 g, 0.029 mole) in 1,2-dichloroethane is treated with BCl$_3$ (3.40 g, 0.029 mole) over a 20 minute period at −8° to 5° C., starred at −2° to 5° C. for 35 minutes, treated with cyclopropylnitrile (2.9 g, 0.043 mole) over a 15 minute period at 0° to 5° C., treated with AlCl$_3$ (4.2 g, 0.0315 mole) in a single portion and stirred at ambient temperatures for 1.5 hours. The reaction mixture is heated at reflux temperature for 18 hours, added to an excess volume of water and stirred for 16 hours. The phases are separated and the aqueous phase is extracted with methylene chloride. The organic phases are combined and concentrated in vacuo to give the title product, 2.55 g, 90% pure, 49.1% yield, identified by HPLC analysis.

EXAMPLE 4

Comparative Preparation of 1-(o-aminophenyl)-4-Chloro-1-Butanone

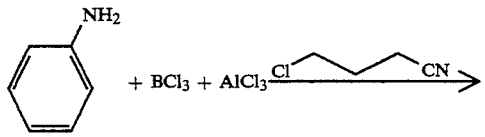

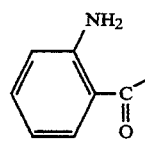

The following procedure is described in U.S. Pat. No. 4,988,695.

To a solution of boron trichloride (55 g) in 1,2-dichloroethane (200 ml) at 0° was added dropwise a solution of aniline (39.1 g, 0.42 mol) in 1,2-dichloroethane (50 ml) maintaining the temperature below 5°. On completion of the addition 4-chlorobutyronitrile (41.4 g, 0.42 mol) and aluminium chloride (53.34 g, 0.42 mol) were added successively and the reaction mixture allowed to warm up to room temperature then heated under reflux for 20 hours. After allowing to cool, 2N hydrochloric acid (100 ml) was added and the reaction mixture heated under reflux for 0.5 hour. The solid obtained was collected by filtration, taken up in water and extracted with chloroform (5×200 ml). The chloroform extracts were combined, washed with dilute base, then water, dried over magnesium sulphate, filtered and evaporated under reduced pressure to give an oil. The oil was dissolved in ether and ethanolic HCl was added, the resulting solid was collected by filtration and dried, 28.5 g, 29% yield. Recrystallization from ethanol/diethylether gave the product hydrochloride salt, m.p. 152°–154° C.

I claim:

1. A process for the manufacture of an o-aminophenyl ketone of formula I

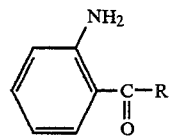

wherein R is C$_3$–C$_6$cycloalkyl or C$_1$–C$_6$haloalkyl which comprises the following steps (1) reacting a nitrile of formula II

R—CN

II with borontrihalide in the presence of a solvent to form a 1:1 donor complex, (2) reacting the complex with aniline in the presence of a Lewis acid to give a reaction mixture, (3) sparging the reaction mixture with an inert gas at an elevated temperature for a period of about 1–24, hours and (4) quenching the sparged reaction mixture with water to give the formula I product.

2. The process according to claim 1 wherein the solvent is dichloropropane or dichloroethane.

3. The process according to claim 2 wherein the solvent is dichloroethane.

4. The process according to claim 1 wherein the borontrihalide is borontrichloride.

5. The process according to claim 1 wherein the Lewis acid is aluminum chloride.

6. The process according to claim 1 wherein the inert gas is nitrogen.

7. The process according to claim 1 wherein the elevated temperature is about 30° C. to 110° C.

8. The process according to claim 1 wherein the sparging period is about 8 to 16 hours.

9. The process according to claim 8 wherein the sparging period is about 12 hours.

10. The process according to claim 1 wherein the molar ratio of formula II compound to aniline is about 1:1 to about 2:1.

11. The process according to claim 10 wherein the molar ratio of formula II compound to aniline is about 1.3:1 to 1.5:1.

12. The process according to claim 1 wherein the nitrile of formula II is cyclopropylnitrile.

13. The process according to claim 1 wherein the nitrile of formula II is 4-halobutyronitrile.

14. The process according to claim 4 wherein the nitrile of formula II is cyclopropylnitrile.

15. The process according to claim 4 wherein the nitrile of formula II is 4-halobutyronitrile.

16. The process according to claim 15 wherein the 4-halobutyronitrile is 4-bromobutyronitrile or 4-chlorobutyronitrile or mixtures thereof.

17. The process according to claim 14 wherein the Lewis acid is aluminum chloride.

18. The process according to claim 15 wherein the Lewis acid is aluminum chloride.

19. The process according to claim 17 wherein the inert gas in nitrogen.

20. The process according to claim 18 wherein the inert gas is nitrogen.

* * * * *